(12) United States Patent
Gross et al.

(10) Patent No.: US 11,669,963 B2
(45) Date of Patent: Jun. 6, 2023

(54) TRACKING OF IMAGE QUALITY IN MAGNETIC RESONANCE IMAGING

(71) Applicant: KONINKLIJKE PHILIPS N.V., Eindhoven (NL)

(72) Inventors: Patrick Gross, Best (NL); Johan Samuel Van Den Brink, Best (NL)

(73) Assignee: Koninklijke Philips N.V., Eindhoven (NL)

(*) Notice: Subject to any disclaimer, the term of this patent is extended or adjusted under 35 U.S.C. 154(b) by 154 days.

(21) Appl. No.: 17/252,757

(22) PCT Filed: Jun. 14, 2019

(86) PCT No.: PCT/EP2019/065680
§ 371 (c)(1),
(2) Date: Dec. 16, 2020

(87) PCT Pub. No.: WO2019/243186
PCT Pub. Date: Dec. 26, 2019

(65) Prior Publication Data
US 2021/0192733 A1 Jun. 24, 2021

(30) Foreign Application Priority Data
Jun. 19, 2018 (EP) .................................. 18178423

(51) Int. Cl.
*G06T 7/00* (2017.01)
*A61B 5/055* (2006.01)
(Continued)

(52) U.S. Cl.
CPC ............ *G06T 7/0012* (2013.01); *A61B 5/055* (2013.01); *G01R 33/5608* (2013.01);
(Continued)

(58) Field of Classification Search
CPC ..... G06T 7/0012; G06T 1/0021; G06T 5/005; G06T 11/60; G06T 2207/30168;
(Continued)

(56) References Cited

U.S. PATENT DOCUMENTS 9,910,111 B2 * 3/2018 Chen .................... G01R 33/543
10,956,011 B2 * 3/2021 Kim .................... G01R 33/546
(Continued)

FOREIGN PATENT DOCUMENTS

EP     1849915 A2 * 10/2007 ............ B42D 25/25
JP     2006280820 A    10/2006

OTHER PUBLICATIONS

Wei Pan et al; "Watermarking to Enforce Medical Image Access and Usage Control Policy", Signal-Image Technology and Internet-Based Systems (SITIS), 2010 Sixth International Conference on, IEEE, Dec. 15, 2010 (Dec. 15, 2010), pp. 251-260, XP031980447, DOI: 10.1109/SITIS.2010.50ISBN:978-1-4244-9527-6abstract p. 251.
(Continued)

*Primary Examiner* — Shefali D Goradia

(57) ABSTRACT

The invention provides for a magnetic resonance imaging system (100) for acquiring magnetic resonance data (144, 146) of a subject (118) within an imaging zone (108), wherein the magnetic resonance imaging system comprises a memory storing a set of parameter ranges (150). At least a portion of the parameter ranges are user configurable. Machine executable instructions cause a processor controlling the magnetic resonance imaging system to: receive (300) configuration commands (152) configured for setting adjustable image acquisition parameters (506) of a pulse sequence recipe; determine (302) if an out of range status exists by determining if any of the configuration commands are outside of the parameter range; provide (304) a warning signal (200) if the out of range status exists; receive (306) a scan status command (156) from a user interface (132);
(Continued)

acquire (308) the magnetic resonance data by controlling the magnetic resonance imaging system using the pulse sequence recipe and the configuration commands if the scan status indicates an acceptance of the out of range status; label (310) the magnetic resonance data with a quality indicator (158); and write (312) the magnetic resonance data with the quality indicator to a computer readable storage medium.

18 Claims, 15 Drawing Sheets

(51) Int. Cl.
    *G01R 33/56*     (2006.01)
    *G06T 1/00*     (2006.01)
    *G06T 5/00*     (2006.01)
    *G06T 11/60*     (2006.01)

(52) U.S. Cl.
    CPC ............ *G06T 1/0021* (2013.01); *G06T 5/005* (2013.01); *G06T 11/60* (2013.01); *G06T 2207/10088* (2013.01); *G06T 2207/30004* (2013.01); *G06T 2207/30168* (2013.01)

(58) Field of Classification Search
    CPC . G06T 2207/30004; G06T 2207/10088; A61B 5/055; G01R 33/5608
    See application file for complete search history.

(56) References Cited

U.S. PATENT DOCUMENTS

| | | |
|---|---|---|
| 2004/0148403 A1 | 7/2004 | Choubey et al. |
| 2009/0290770 A1 | 11/2009 | Mori et al. |
| 2011/0113376 A1 | 5/2011 | Suzuki et al. |
| 2015/0286780 A1 | 10/2015 | Saybasili et al. |
| 2016/0231396 A1* | 8/2016 | Sunaga ................ G01R 33/288 |
| 2017/0156630 A1 | 6/2017 | Gabr et al. |

OTHER PUBLICATIONS

International Search Report and Written Opinion From PCT/EP2019/065680 dated Oct. 9, 2019.

* cited by examiner

TRACKING OF IMAGE QUALITY IN MAGNETIC RESONANCE IMAGING

CROSS REFERENCE TO RELATED APPLICATIONS

This application is a U.S. national phase application of International Application No. PCT/EP2019/065680 filed on Jun. 14, 2019 which claims the benefit of EP Application Serial No. 18178423.2 filed on Jun. 19, 2018 and is incorporated herein by reference.

FIELD OF THE INVENTION

The invention relates to magnetic resonance imaging.

BACKGROUND OF THE INVENTION

A large static magnetic field is used by Magnetic Resonance Imaging (MRI) scanners to align the nuclear spins of atoms as part of the procedure for producing images within the body of a subject. This large static magnetic field is referred to as the B0 field or the main magnetic field. Various quantities or properties of the subject can be measured spatially using MRI. Various imaging protocols can be implemented by using pulse sequences to control the acquisition of magnetic resonance data. In the design of these pulse sequences there are typically a large number of adjustable image acquisition parameters. In clinical settings various standards exist for allowed ranges for the adjustable image acquisition parameters.

United States Patent Application Publication US 2011/0113376 discloses a scan condition setting apparatus that sets a scan condition used upon scanning a subject. The apparatus includes a selection device having a plurality of combinations of scan times and image quality and that selects one from within the plurality combinations according to a manipulation of an operator, and a scan condition storage device for storing scan conditions corresponding to the combinations of the scan times and image quality therein. The scan condition corresponding to the combination of the scan times and image quality selected by the selection device is set as the scan condition used when the subject is scanned.

United States Patent Application Publication US 2017/0156630 discloses a protocol optimization system that is configured to, based on an input of an optimized protocol definition, access a data store, containing a plurality of optimized protocol definitions, to identify a scout MRI scan.

SUMMARY OF THE INVENTION

The invention provides for a magnetic resonance imaging system, a computer-readable storage medium storing magnetic resonance data, and a medical imaging system in the independent claims. Embodiments are given in the dependent claims.

Magnetic resonance imaging systems typically have hard coded values for adjustable image acquisition parameters in example pulse sequences of magnetic resonance imaging protocols. The operator of the magnetic resonance imaging system can select a magnetic resonance imaging protocol and then modify the adjustable image acquisition parameters of the example pulse sequence. As was mentioned above there may be various standards or best practices for which range of values the adjustable image acquisition parameters may be set to. Often if the adjustable image acquisition parameters set to values outside of an allowed or accepted range then the image should not be used for diagnosis.

Embodiments may provide for a means of reducing the risk that an image which was acquired with adjustable image acquisition parameters is outside of an acceptable range is accidentally used. Embodiments check if the adjustable image acquisition parameters have values that are within a set of parameters ranges. Adjustable image acquisition parameters may have their own parameter range which their value can be checked against.

If an adjustable image acquisition parameter is out of range, then the magnetic resonance imaging system may provide a warning signal to alert the operator. The operator can then decide to proceed even with the warning or take an alternative action like adjusting the adjustable image acquisition parameters so that their values are within their parameter range. If the operator decides to proceed with acquisition of magnetic resonance data, even with a warning signal, then the magnetic resonance data is labeled with a quality indicator.

The quality indicator could take different forms in different examples. The quality indicator could be metadata inserted into a header of the magnetic resonance data. The quality indicator could also be data used to intentionally corrupt the data and/provide a visible indicator.

In one aspect the invention provides for a magnetic resonance imaging system for acquiring magnetic resonance data of a subject within an imaging zone. As used herein magnetic resonance data may refer to either magnetic resonance imaging data or magnetic resonance k-space data. The magnetic resonance imaging system comprises a memory for storing machine-executable instructions. The memory is further storing one or more pulse sequence recipes configured for controlling the magnetic resonance imaging system to acquire the magnetic resonance data. The pulse sequence recipes may each also be considered to be a description of a magnetic resonance imaging protocol. The pulse sequence recipe is data descriptive of the actions taken by various components of the magnetic resonance imaging system as a function of time. The pulse sequence recipe can be converted into executable commands to control the components of the magnetic resonance imaging system either before beginning the acquisition of the magnetic resonance data or on the fly.

The memory further stores a set of parameter ranges. At least a portion of the parameter ranges are user configurable. For example, the parameter ranges may be stored within a file or memory such that they can be altered by a user. The one or more pulse sequence recipes are configured for having one or more adjustable image acquisition parameters. The adjustable image acquisition parameters are adjustable parameters which affect how the magnetic resonance data is acquired. For example, this may include such qualities as the repetition time, the flip angle or other parameters which are used to modify a pulse sequence. The adjustable image acquisition parameters may vary from pulse sequence recipe to pulse sequence recipe. The set of parameter ranges comprises a parameter range for each of the one or more adjustable image acquisition parameters. In some cases, each of the one or more adjustable image acquisition parameters may be set to a default value.

The magnetic resonance imaging system further comprises a processor configured for controlling the magnetic resonance imaging system. Execution of the machine-executable instructions causes the processor to receive configuration commands configured for setting the adjustable image acquisition parameters of a pulse sequence recipe selected from the one or more pulse sequence recipes. They may for example be received via a user interface or they may be received via other technical means such as via a computer storage medium or over a network. Execution of the machine-executable instructions further causes the processor to determine if an out of range status exists by determining if any of the configuration commands are outside of the parameter range.

Execution of the machine-executable instructions further causes the processor to provide a warning signal if the out of range status exists. The warning signal may for example be an audio or visual signal which is used to warn the operator of the magnetic resonance imaging system that the out of range status exists. In some examples the warning signal may be a dialogue box provided on a user interface or display. Execution of the machine-executable instructions further causes the processor to receive a scan status command from the user interface. This may be in response to the providing of a warning signal. The scan status command may for example be an instruction relating to the providing of the warning signal.

Execution of the machine-executable instructions further causes the processor to acquire the magnetic resonance data by controlling the magnetic resonance imaging system using the pulse sequence recipe and the configuration commands if the scan status command indicates an acceptance of the out of range status. The configuration commands and the pulse sequence recipe can be used to generate executable commands for controlling the components of the magnetic resonance imaging system before beginning the acquisition or they can be generated on the fly.

The magnetic resonance imaging system is configured to acquire the magnetic resonance data even if the out of range status exists as long as the scan status command is received and indicates an acceptance of this out of range status. If the scan status does not indicate an acceptance of the out of range status there are a variety of other responses. For example, the user may be prompted to further adjust the configuration commands or it may also result in the cancelling of the magnetic resonance imaging scan. Execution of the machine-executable instructions further cause the processor to label the magnetic resonance data with a quality indicator. Execution of the machine-executable instructions further cause the processor to write the magnetic resonance data with the quality indicator to a computer-readable storage medium.

This embodiment may be beneficial because the marking of the magnetic resonance data with the quality indicator may be useful for identifying if the magnetic resonance data was acquired according to particular quality standards or specifications or not. For example, it may be possible that during the course of a magnetic resonance imaging examination the pulse sequence parameters are changed. The system is able to check if the one or more adjustable image acquisition parameters will be within the parameter range or not before the magnetic resonance data is acquired.

The operator may receive a warning signal if all of the adjustable image acquisition parameters are not within their particular parameter range. The operator can then decide to accept this condition or not. If the condition is accepted then the magnetic resonance data is then labeled with the quality indicator so that someone else examining the magnetic resonance data later will not use magnetic resonance data that was acquired properly and potentially make a wrong diagnosis. This may provide for example for greater security.

An advantage of this embodiment is that at least a portion of the parameter ranges are user configurable. In current systems such ranges may be non-existent or may be hard-wired such as incorporated into the source code for the magnetic resonance imaging system. Making the parameter ranges user configurable may enable the use or finer control of adjustable image acquisition parameters such that they meet certain safety and/or image quality requirements.

In another embodiment the quality indicator is configured for causing a visible indicator in the magnetic resonance data. For example, the quality indicator may result in an intentional corruption of the magnetic resonance data or may cause a visual indicator such as a marking or warning or obscuring a part of the magnetic resonance data to alert a healthcare professional who is examining the magnetic resonance data. This for example may be beneficial because it may prevent the unintentional use of magnetic resonance data that was not acquired according to particular safety and/or image quality standards.

This embodiment may also have the additional benefit that it may force the user to use the proper software. For example, in many clinical situations the so called DICOM standard is used for storing images. Various data may be contained within a particular DICOM header. A difficulty is that data with a DICOM header can simply be ignored. If a DICOM viewing software is used from a different vendor or if old software is used it may not be able to detect or warn a healthcare professional if a flag is set that indicates that an image should not be used for diagnostic purposes. Causing the visible indicator may prevent the misuse of magnetic resonance data and may for example provide for improved safety by eliminating the possibility of a false diagnosis.

In another embodiment the visual indicator is configured to do any one of the following: obscure a portion of the magnetic resonance image data, place a symbol in the magnetic resonance imaging data, place a text message in the magnetic resonance data, corrupt the magnetic resonance data in a reversible fashion, and combinations thereof. This may be beneficial because as was mentioned above the providing of a visual indicator may provide a warning to a healthcare professional even when the proper viewing software is not used.

In another embodiment the magnetic resonance data is magnetic resonance k-space data. The magnetic resonance data is labeled by writing the quality indicator to a predetermined location in k-space within the magnetic resonance data. Writing data intentionally into the k-space data may cause a magnetic resonance image to be intentionally corrupted. This may prevent a healthcare professional from using unauthorized software to reconstruct a magnetic resonance image from the magnetic resonance k-space data.

In some examples of this the magnetic resonance data may have a header. Instructions on how to retrieve or remove the quality indicator from the magnetic resonance k-space data may be included in this header.

In some examples the magnetic resonance k-space data may be intentionally modified causing it to have a recognizable watermark such as text, a symbol or geometric lines that are caused in the resulting magnetic resonance image.

In another embodiment the magnetic resonance data is magnetic resonance image data. The magnetic resonance image data is a data which may be used to directly render a magnetic resonance image.

In another embodiment the quality indicator comprises watermark data configured for generating a visible watermark. In this example the visible indicator may be a visible watermark. The visible watermark may be constructed such that it is difficult to remove from the magnetic resonance image data. This again may provide a means for alerting a healthcare professional when a viewing program that cannot detect the quality indicator is used. Various methods may be used for constructing the visible watermark such as wavelet, modification of specific pixels or other methods. The generation of the visible watermark may also be used to obscure portions or make them less readable. This may for example be used to force a healthcare professional to use a particular viewing program or software.

In another embodiment the magnetic resonance data comprises a header. Execution of the machine-executable instructions further causes the processor to write visible indicator removal data descriptive or instructions on how to remove the visible indicator to the header. For example, if the visible indicator is a watermark, an image space or data which has been intentionally added to k-space to corrupt the k-space the visible indicator removal data may be used to provide instructions as to how to remove this. In some examples the removal of the corrupted k-space data or the removal of the watermark may involve a relatively complicated or cryptographic algorithm. The visual indicator removal data for example may be a key or data which may enable the removal of the visible indicator.

In another embodiment the header is a DICOM header.

In another embodiment the quality indicator comprises a presentation state which is used to overlay a magnetic resonance image. For example, the quality indicator can be constructed such that it obscures a portion of the image or provides a warning to the healthcare professional.

In another embodiment execution of the machine-executable instructions further causes the processor to write a quality indicator to the header. The quality header is descriptive of if any of the one or more adjustable image acquisition parameters is outside of their parameter range. For example, in addition to providing the visible indicator specific data on the pulse sequence recipe and in particular which of the adjustable image acquisition parameters are out of range may be explicitly placed into the header.

In another embodiment the magnetic resonance imaging system further comprises a display. Execution of the machine-executable instructions further causes the processor to display a parameter range change dialogue box on the display. The parameter range change dialogue box is configured for receiving range change data descriptive of changes to the predetermined range for the one or more adjustable image acquisition parameters for a pulse sequence recipe selected from the one or more pulse sequence recipes. Execution of the machine-executable instructions further causes the processor to receive the range change data from the dialogue box.

Execution of the machine-executable instructions further causes the processor to modify the predetermined range for each of the one or more adjustable image acquisition parameters using the range change data. This embodiment may be beneficial because it may provide for a means of changing the set of parameter ranges which may be normally hard-wired into the source code for the system operating the magnetic resonance imaging system.

An alternative to the use of a parameter range change dialogue box may be a text or other data file such as an XML file which can be manually edited to change or adjust the set of parameter ranges.

In some embodiments the display could also be used for providing the warning signal. For example, in the form of a pop-up dialogue box which is provided on the display or user interface.

In another embodiment, the adjustable parameters comprise a pulse sequence recipe identifier. Where the range change data comprises a modified identifier. The parameter range change dialogue box is configured for receiving a modified identifier descriptive of a change to the recipe identifier. Execution of the machine-executable instructions further causes the processor to receive the modified identifier from the from the parameter range change dialogue box.

In another embodiment the predetermined range for each of the one or more adjustable image acquisition parameters may be stored in a configuration file.

In another aspect the invention provides for a computer-readable storage medium storing magnetic resonance data. The magnetic resonance data is configured for being rendered as a magnetic resonance image or for being reconstructed into the magnetic resonance image. For example, the magnetic resonance data may either be data which is stored in image space or in k-space. The magnetic resonance data comprises a quality indicator configured for causing a visible indicator in the magnetic resonance image. This may be useful in alerting a subject when the magnetic resonance data was not acquired according to particular safety and/or image quality standards.

In another embodiment the quality indicator is descriptive if image acquisition parameters used for acquiring the labeled magnetic resonance data were outside of a parameter range.

In another embodiment the visible indicator is configured for being removable from the magnetic resonance data. For example, the computer-readable storage medium may in a header or other means store instructions for removing the quality indicator or for suppressing it.

In another embodiment the magnetic resonance data is magnetic resonance k-space data. The quality indicator is stored in a predetermined location in k-space within the magnetic resonance data. The predetermined location may for example be a particular location in k-space or may be distributed locations according to the use of an algorithm. In this example the quality indicator is used to intentionally corrupt the magnetic resonance k-space data.

In another embodiment the magnetic resonance data is magnetic resonance image data. The quality indicator is configured to do any one of the following: obscure a predefined portion of the magnetic resonance image data, place a symbol in the magnetic resonance image data, place a text message in the magnetic resonance image data, corrupt at least a portion of the magnetic resonance image, place a text message in the magnetic resonance image data containing a pulse sequence recipe identifier, and combinations thereof. This for example may be useful in alerting a healthcare professional when proper viewing software is not used or available.

In another embodiment the quality indicator is data or a configuration of a presentation state in a DICOM header.

In another embodiment the quality indicator comprises watermark data configured for causing a visible watermark within the magnetic resonance image data. The advantages of this have been previously discussed.

In another embodiment the magnetic resonance data comprises a header. The header comprises quality indicator removal data descriptive of removal of the watermark data to the header.

In another aspect the invention provides for a medical imaging system comprising an imaging system memory and an imaging system processor. The imaging system memory stores machine-executable instructions. Execution of the machine-executable instructions causes the imaging system processor to receive magnetic resonance data configured for being rendered as a magnetic resonance image or for being reconstructed into the magnetic resonance image. The magnetic resonance data comprises a quality indicator descriptive of whether one or more of the pulse sequence modification commands that are used to acquire the magnetic resonance data are outside of predetermined range. The quality indicator is configured for causing a visible indicator in the magnetic resonance image. Execution of the machine-executable instructions further causes the processor to calculate modified magnetic resonance data by removing the visible indicator from the magnetic resonance image.

Execution of the machine-executable instructions further causes the processor to render the magnetic resonance image data without the visible indicator on a display using the modified magnetic resonance data. This may be beneficial because it may provide a means for the healthcare professional to view the image without the visible indicator. Additional functionality may also be included such as the automatic inclusion of a warning on the user interface but that does not obstruct or modify the magnetic resonance image.

In another embodiment the modified magnetic resonance data is stored in a non-persistent memory. For example, after the magnetic resonance image is displayed the system may automatically delete the modified magnetic resonance data so that it is not stored in the modified form. This may for example prevent the visible indicator from being permanently stripped from the data.

In another aspect the invention provides for a computer readable storage medium comprising machine executable instructions for execution by a processor controlling a magnetic resonance imaging system configured for acquiring magnetic resonance data of a subject within an imaging zone.

The magnetic resonance imaging system comprises a processor configured for controlling the magnetic resonance imaging system. Execution of the machine executable instructions causes a processor configured to control the magnetic resonance imaging system to receive configuration commands configured for setting the adjustable image acquisition parameters of pulse sequence recipe configured is for controlling the magnetic resonance imaging system to acquire the magnetic resonance data according to a magnetic resonance imaging protocol. The computer readable storage medium further memory further stores a set of parameter ranges. At least a portion of the parameter ranges are user configurable. The pulse sequence recipe is configured for having one or more adjustable image acquisition parameters. The set of parameter ranges comprises a parameter range for the one or more adjustable image acquisition parameters. Execution of the machine executable instructions further cause the processor to determine if an out of range status exists by determining if any of the configuration commands are outside of the parameter range.

Execution of the machine executable instructions further cause the processor to provide a warning signal if the out of range status exists. Execution of the machine executable instructions further cause the processor to receive a scan status command from a user interface. Execution of the machine executable instructions further cause the processor to acquire the magnetic resonance data by controlling the magnetic resonance imaging system using the pulse sequence recipe and the configuration commands if the scan status indicates an acceptance of the out of range status. Execution of the machine executable instructions further cause the processor to label the magnetic resonance data with a quality indicator. Execution of the machine executable instructions further cause the processor to write the magnetic resonance data with the quality indicator to a computer readable storage medium.

In another aspect the invention provides for a method of operating a magnetic resonance imaging system. The method comprises receiving configuration commands configured for setting the adjustable image acquisition parameters of pulse sequence recipe. The pulse sequence recipe configured for controlling the magnetic resonance imaging system to acquire the magnetic resonance data according to a magnetic resonance imaging protocol. A memory stores a set of parameter ranges. At least a portion of the parameter ranges are user configurable. The pulse sequence recipe is configured for having one or more adjustable image acquisition parameters. The set of parameter ranges comprises a parameter range for the one or more adjustable image acquisition parameters.

The method further comprises determining if an out of range status exists by determining if any of the configuration commands are outside of the parameter range. The method further comprises providing a warning signal if the out of range status exists. The method comprises receiving a scan status command from a user interface. The method further comprises acquiring the magnetic resonance data by controlling the magnetic resonance imaging system using the pulse sequence recipe and the configuration commands if the scan status indicates an acceptance of the out of range status. The method further comprises label the magnetic resonance data with a quality indicator. The method further comprises the magnetic resonance data with the quality indicator to a computer readable storage medium.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic resonance k-space data is defined herein as being the recorded measurements of radio frequency signals emitted by atomic spins using the antenna of a Magnetic resonance apparatus during a magnetic resonance imaging scan.

The magnetic resonance k-space data may be reconstructed into Magnetic resonance image data. The magnetic resonance image data may be two or three-dimensional image data that can be rendered as an image. The magnetic resonance image data may also be referred to as a Magnetic Resonance image or MR image.

The term magnetic resonance data as used herein refers to either magnetic resonance k-space data or magnetic resonance image data.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
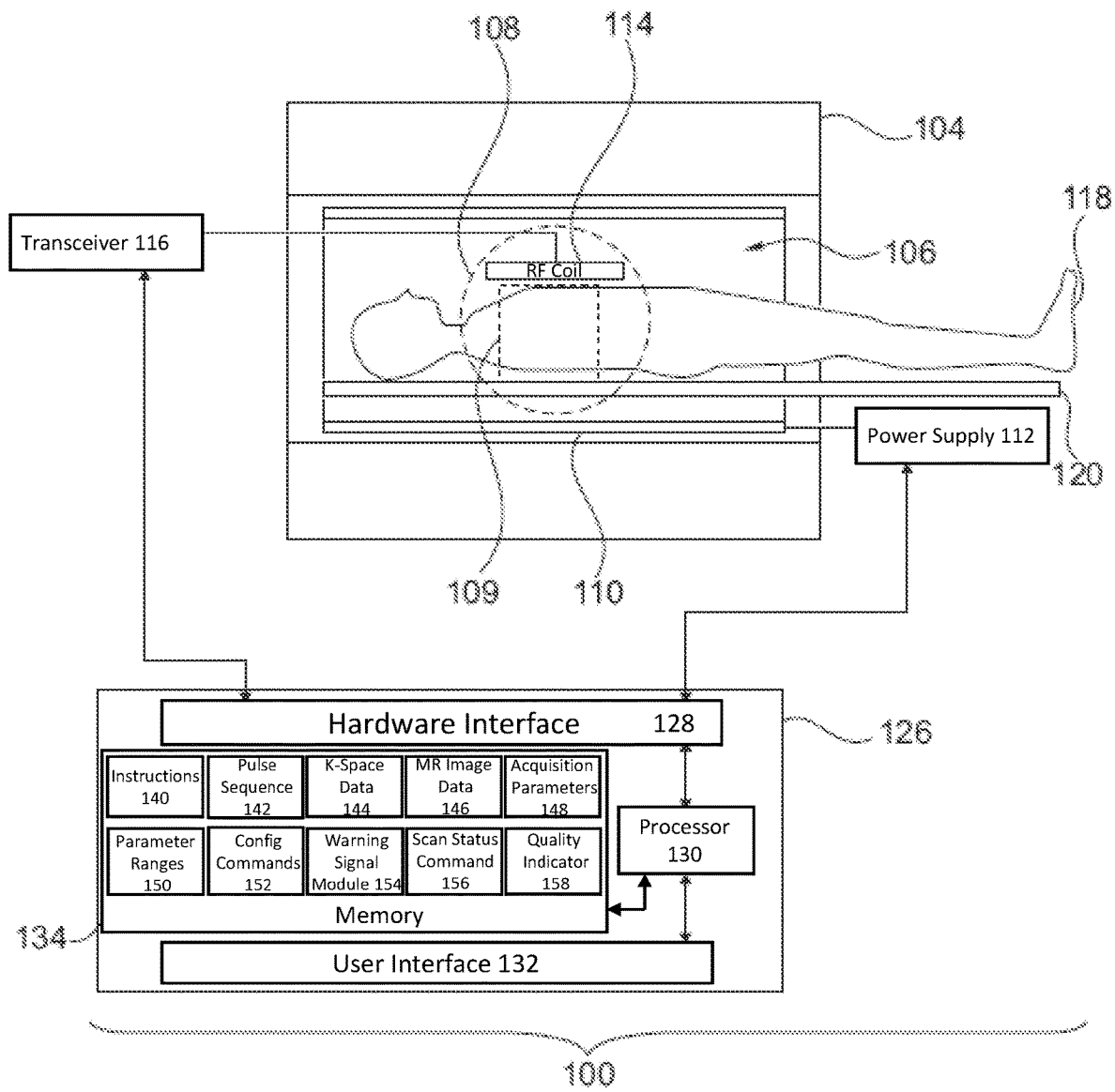
FIG. 1 illustrates an example of a magnetic resonance imaging system.

FIG. 1 shows an example of a magnetic resonance imaging system 100 with a magnet 104. The magnet 104 is a superconducting cylindrical type magnet with a bore 106 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging. A region of interest 109 is shown within the imaging zone 108. The magnetic resonance data that is acquired typically acquired for the region of interest. A subject 118 is shown as being supported by a subject support 120 such that at least a portion of the subject 118 is within the imaging zone 108 and the region of interest 109.

Within the bore 106 of the magnet there is also a set of magnetic field gradient coils 110 which is used for acquisition of preliminary magnetic resonance data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for manipulating the orientations of magnetic spins within the imaging zone 108 and for receiving radio transmissions from spins also within the imaging zone 108. The radio frequency antenna may contain multiple coil elements. The radio frequency antenna may also be referred to as a channel or antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio frequency transceiver 116 are representative. The radio-frequency coil 114 is intended to also represent a dedicated transmit antenna and a dedicated receive antenna. Likewise the transceiver 116 may also represent a separate transmitter and receivers. The radio-frequency coil 114 may also have multiple receive/ transmit elements and the radio frequency transceiver 116 may have multiple receive/transmit channels. For example if a parallel imaging technique such as SENSE is performed, the radio-frequency could 114 will have multiple coil elements.

The transceiver 116 and the gradient controller 112 are shown as being connected to a hardware interface 128 of a computer system 126. The computer system further comprises a processor 130 that is in communication with the hardware system 128, a memory 134, and a user interface 132. The memory 134 may be any combination of memory which is accessible to the processor 130. This may include such things as main memory, cached memory, and also non-volatile memory such as flash RAM, hard drives, or other storage devices. In some examples the memory 134 may be considered to be a non-transitory computer-readable medium.

The memory 134 is shown as containing machine-executable instructions 140. The machine-executable instructions 140 enable the processor 130 to control the operation and function of the magnetic resonance imaging system 100. The machine-executable instructions 140 may also enable the processor 130 to perform various data analysis and calculation functions. The computer memory 134 is further shown as containing pulse sequence recipe 142. The pulse sequence recipe are configured for controlling the magnetic resonance imaging system 100 to acquire magnetic resonance data from the subject 118 according to a magnetic resonance imaging protocol. The pulse sequence recipe can be considered to be the implementation of a pulse sequence. The memory 134 is further shown as containing magnetic resonance k-space data 144 that was acquired by executing the pulse sequence recipe 142. The memory 134 is further shown as containing a magnetic resonance image data 146. The magnetic resonance k-space data 144 and the magnetic resonance image data 146 are both forms of magnetic resonance data. The magnetic resonance image data 146 is a reconstruction of data which can be rendered into an image from the magnetic resonance k-space data 144.

The memory 134 is further shown as containing adjustable image acquisition parameters 148. The adjustable image acquisition parameters 148 are values or configuration data which can be used for modifying or controlling the pulse sequence recipe 142. The memory 134 is further shown as containing a set of parameter ranges 150. The set of parameter ranges 150 are parameter ranges which indicate allowed values or ranges of values that the adjustable image acquisition parameters 148 can take. The memory 134 is further shown as containing configuration commands 152. The configuration commands 152 are commands which are received which are used to either set or adjust the values of the adjustable image acquisition parameters 148.

The memory 134 is further shown as containing a warning signal module 154 that is able to generate a warning signal when the configuration commands 152 would cause the adjustable image acquisition parameters 148 to be set to values outside of what is allowed by the set of parameter ranges 150. If the warning signal is produced by the warning signal module 154 the operator still has the option of acquiring the magnetic resonance k-space data 144 anyway. A user interface 132 can be used to provide a scan status command 156. The scan status command 156 may indicate an acceptance of an out of range status. If this is the case then the processor 130 continues and controls the magnetic resonance imaging system 100 to acquire the magnetic resonance k-space data 144 using the pulse sequence recipe 142. After this has happened either the magnetic resonance k-space data 144 or the magnetic resonance image data has a label attached to it. The label is the quality indicator 158.

The quality indicator 158 is descriptive of the adjustable image acquisition parameters 148. For example, the quality indicator 158 may list the values that were used for the adjustable image acquisition parameters and/or they may indicate which the adjustable image acquisition parameters were outside of the set of parameter ranges 150.

Figure 2:
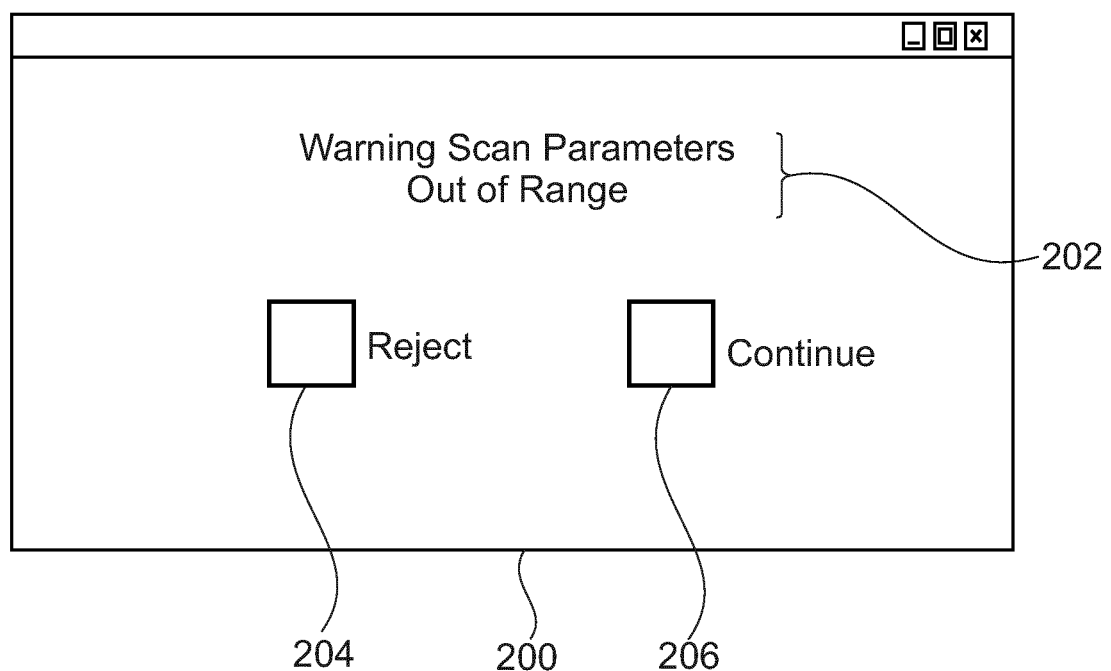
FIG. 2 illustrates an example of a dialogue box.

FIG. 2 illustrates an example of a warning dialogue box 200. The warning dialogue box 200 is an example of a signal generated by the warning signal module 154. The warning dialogue box 200 may provide a warning indicating that one or more scan parameters are out of range. The warning dialogue box 200 may then provide several controls to enable the operator to make a selection. In this example there is a reject button 204 and a continue button 206. When the reject button 204 is pressed or selected it may cause the acquisition of the magnetic resonance data to be cancelled or it may prompt the user to correct some of the values that are out of range. The continue button 206 when pressed or selected may then cause the machine-executable instructions to acquire the magnetic resonance data 144 by controlling the magnetic resonance imaging system with the pulse sequence recipe 142.

Figure 3:
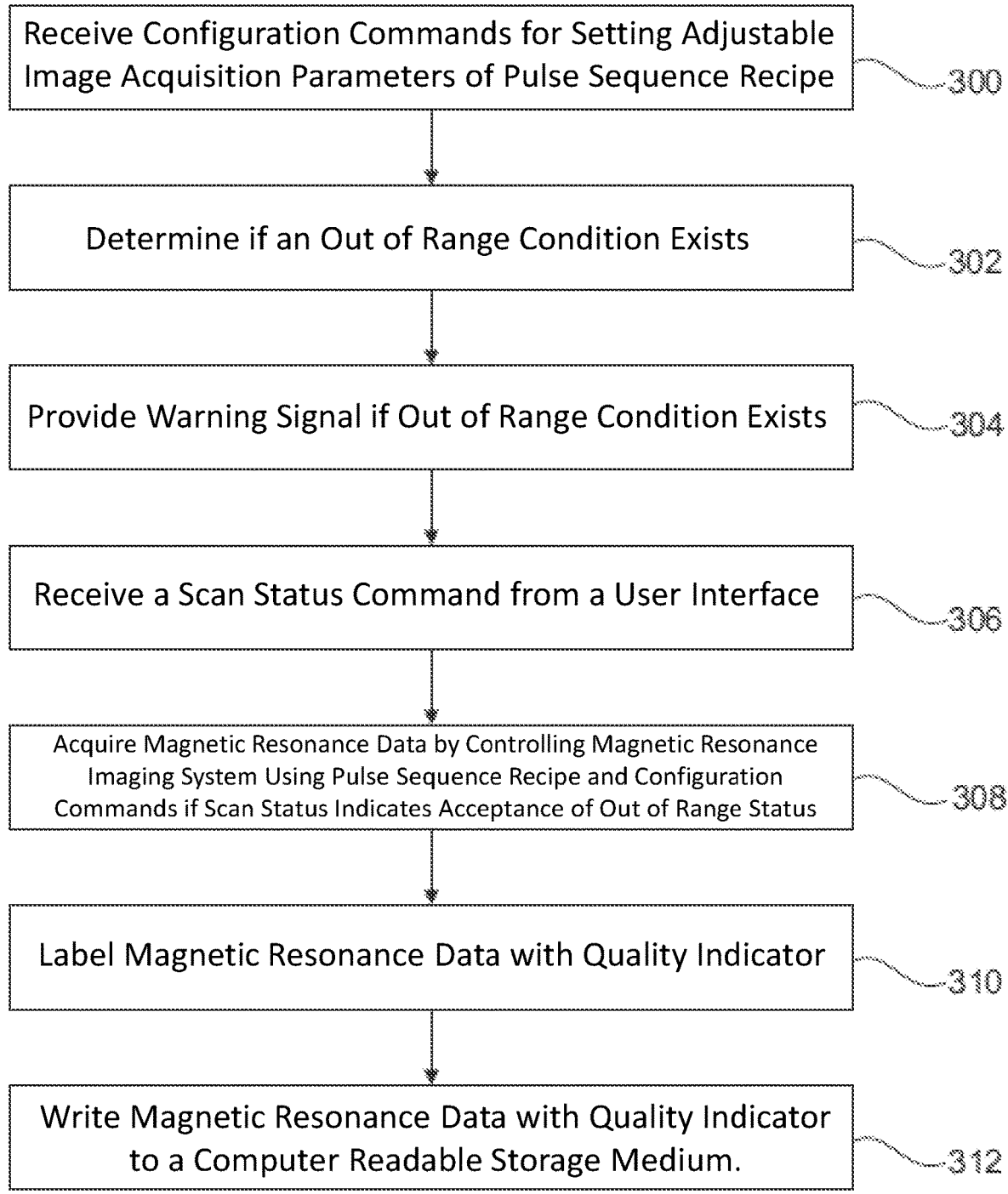
FIG. 3 shows a flow chart which illustrates a method of operating the magnetic resonance imaging system of FIG. 1.

FIG. 3 shows a flowchart which illustrates a method of operating the magnetic resonance imaging system illustrated in FIG. 1. First in step 300 the configuration commands 152 are received. Next in step 302 it is determined if an out of range status exists by determining if any of the configuration commands 152 are outside of the associated parameter range of the set of parameter ranges 150. Then in step 306 a scan status command 156 is received. The scan status command may indicate an acceptance or rejection of the out of range status. Next in step 308 the magnetic resonance imaging system 100 acquires the magnetic resonance k-space data 144 by controlling the magnetic resonance imaging system 100 with the pulse sequence recipe 142 if the scan status indicates an acceptance of the out of range status.

Next in step 310 the magnetic resonance data which would be either the magnetic resonance k-space data 144 or the magnetic resonance image data 146 with a quality indicator 158. The magnetic resonance data 144 or 146 is then written to a computer-readable storage medium 134 with the quality indicator 158. The magnetic resonance data 144 or 146 may take different forms, for example the magnetic resonance data 144, 146 may be encapsulated in a DICOM file.

Figure 4:
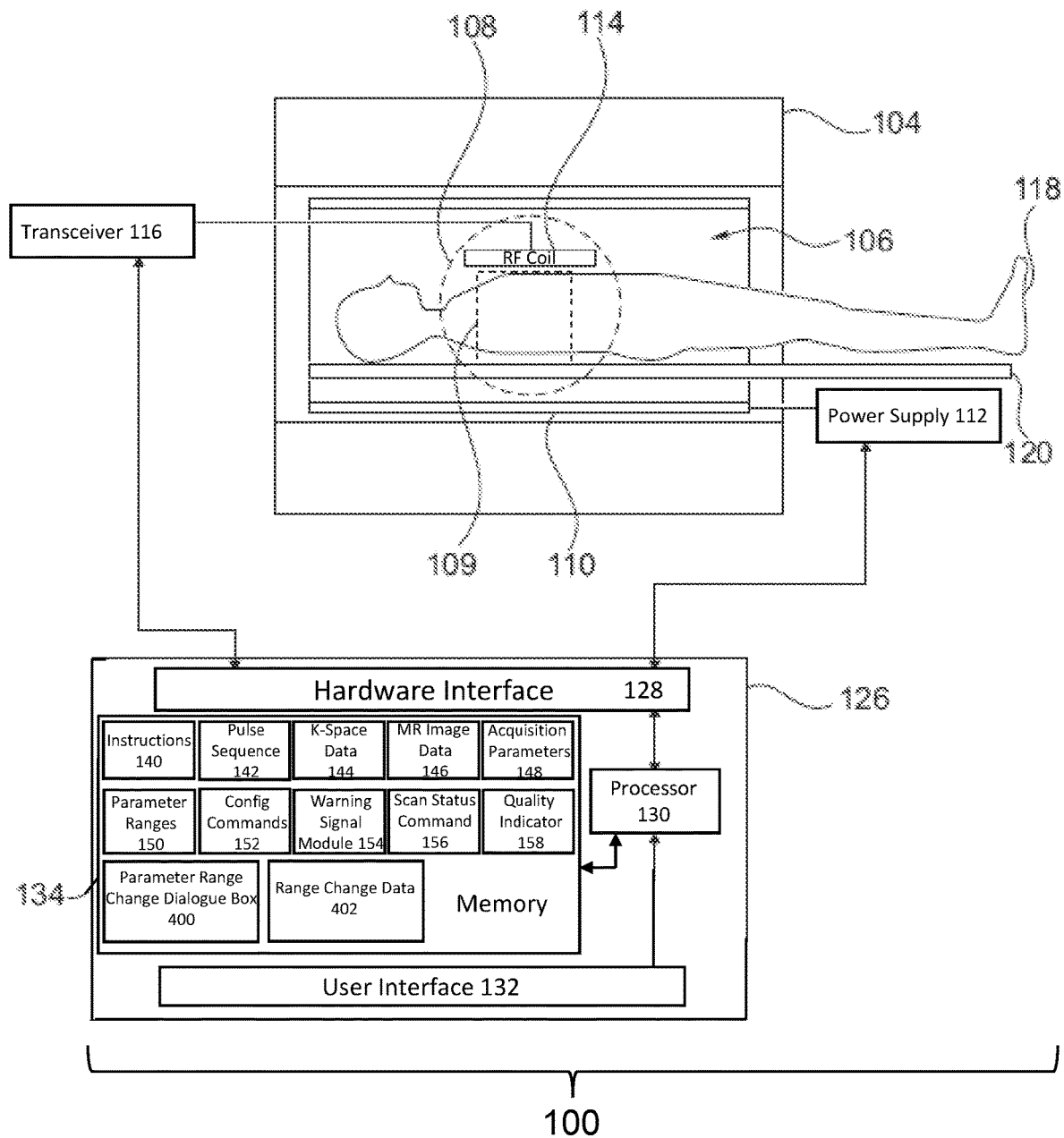
FIG. 4 shows a further view of the magnetic resonance imaging system of FIG. 1.

FIG. 4 shows a further view of the magnetic resonance imaging system 100 from FIG. 1. Several additional software components are shown in the computer memory 134. In the example of FIG. 4 the user interface 134 comprises a display. The memory 134 is shown as additionally containing a parameter range change dialogue box module 400. This software module 400 enables the processor 130 to render and control a parameter range change dialogue box on a display 132. The processor may receive range change data 402 from the parameter range change dialogue box 400.

Figure 5:
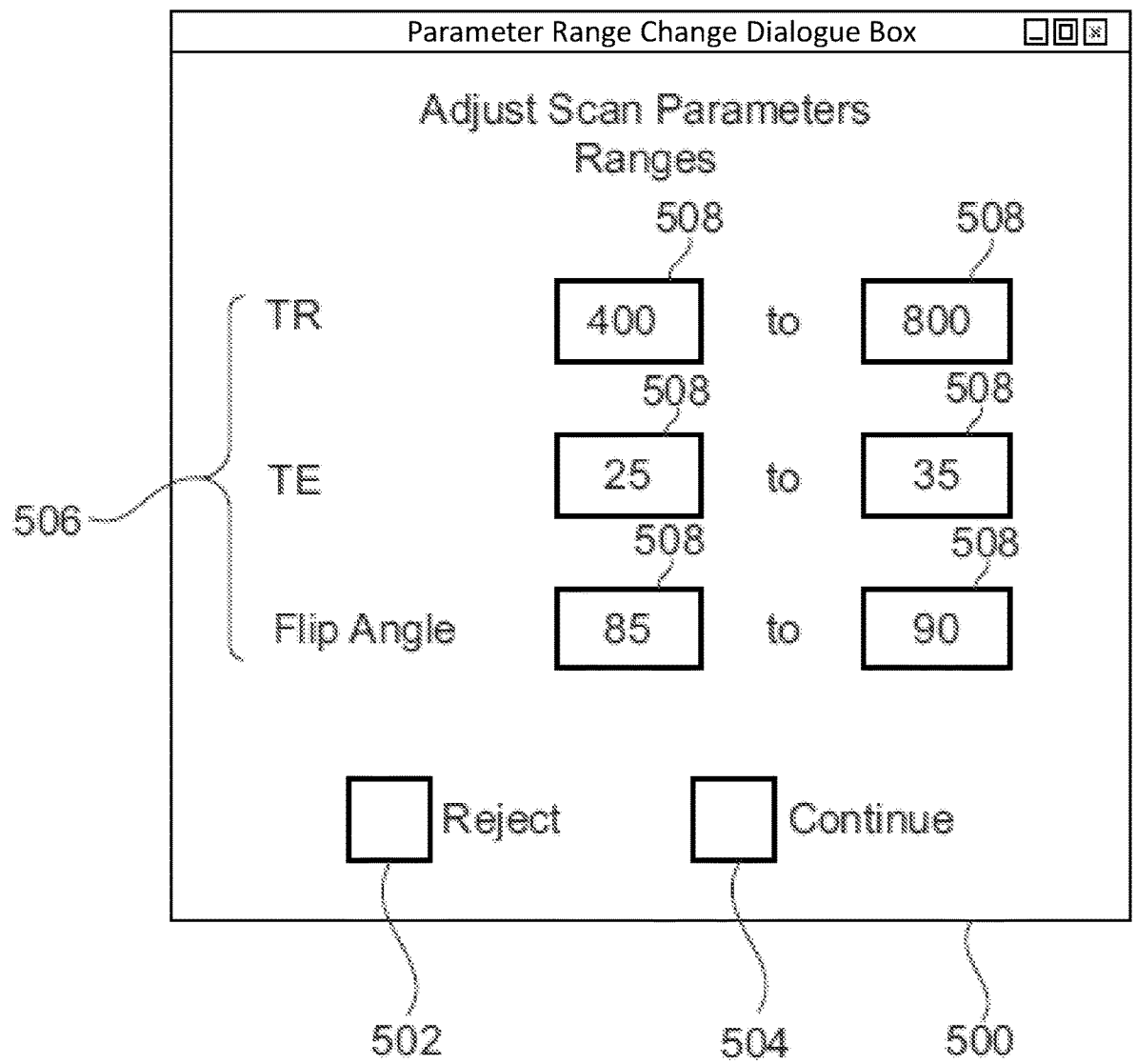
FIG. 5 illustrates a further example of a dialogue box.

FIG. 5 illustrates an example of a parameter range change dialogue box 500. The example parameter range change dialogue box 500 has a number of controls. There is a reject button 502 and a continue button 504. When the reject button 502 is pressed any changes made in the dialogue box 500 are ignored. When the continue button 504 is depressed it sends the range change data 402 to the processor 130. In this example a number of adjustable image acquisition parameters 506 are listed. In this example these are the echo time te, the repetition time gr and the flip angle. The adjustable image acquisition parameters 506 would vary on the particular type of magnetic resonance imaging protocol. For each of the adjustable image acquisition parameters 506 there is a number of boxes 508 to enter a parameter range. In other examples sliders or other controls may also be used.

Figure 6:
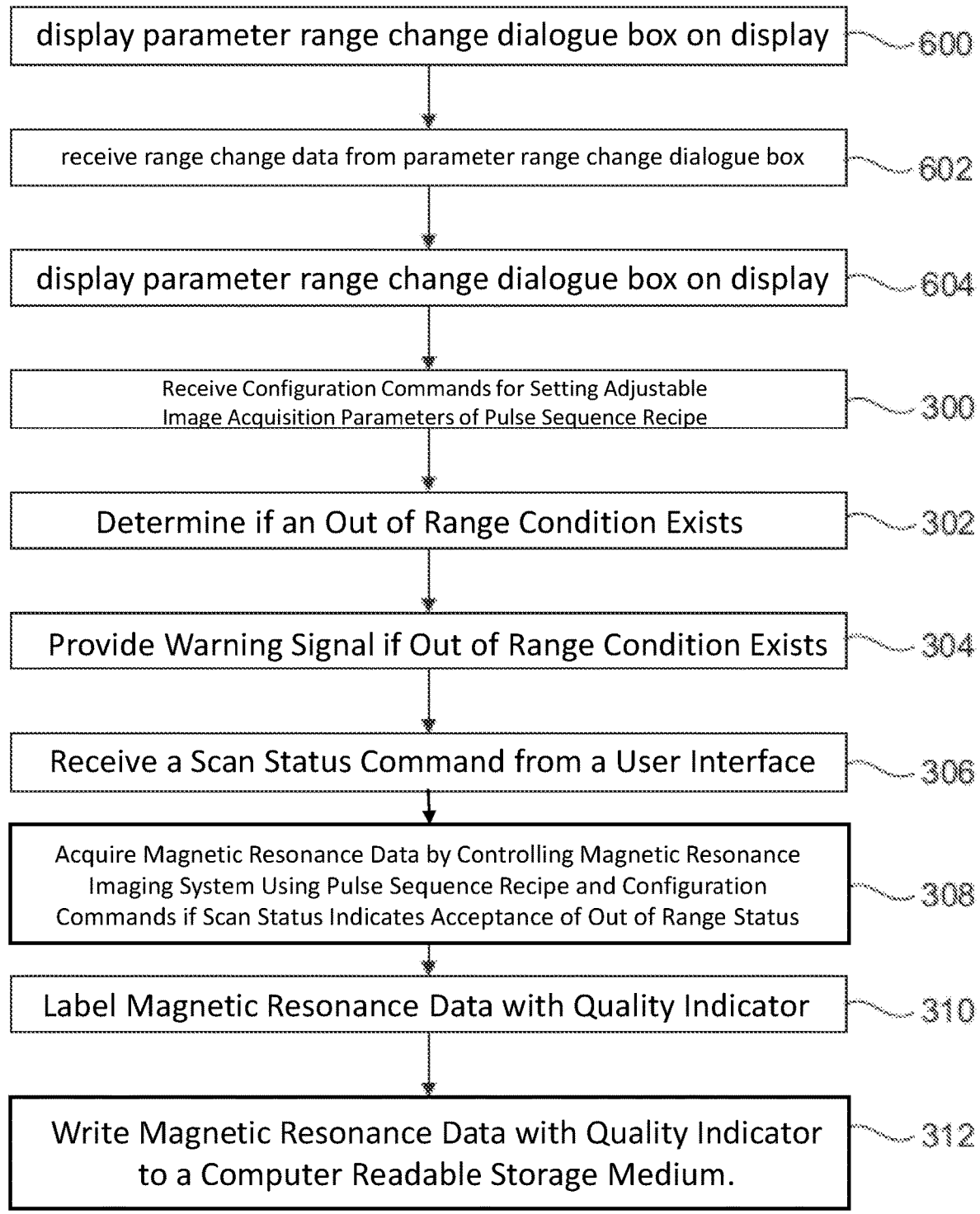
FIG. 6 shows a flow chart which illustrates a method of operating the magnetic resonance imaging system of FIG. 4.

FIG. 6 shows a flowchart which illustrates a method of operating the magnetic resonance imaging system 100 as is illustrated in FIG. 4. First in step 600 the parameter range change dialogue box 500 is displayed on the display of the user interface 132. Next in steps 602 the range change data 402 is received from the parameter range change dialogue box 500. Next in step 604 the predetermined range for each of the one or more adjustable image acquisition parameters is modified using the range change data 402. The range change data 402 is used to modify the set of parameter ranges 150. There could be technical means to limit access to the parameter range change dialogue box 500. For example, access to the parameter range change dialogue box could be protected with a password or a cryptographic key. This may, for example, be used to limit access to the parameter range change dialogue box to qualified experts and prevent routine operators from altering the parameter ranges.

Figure 7:
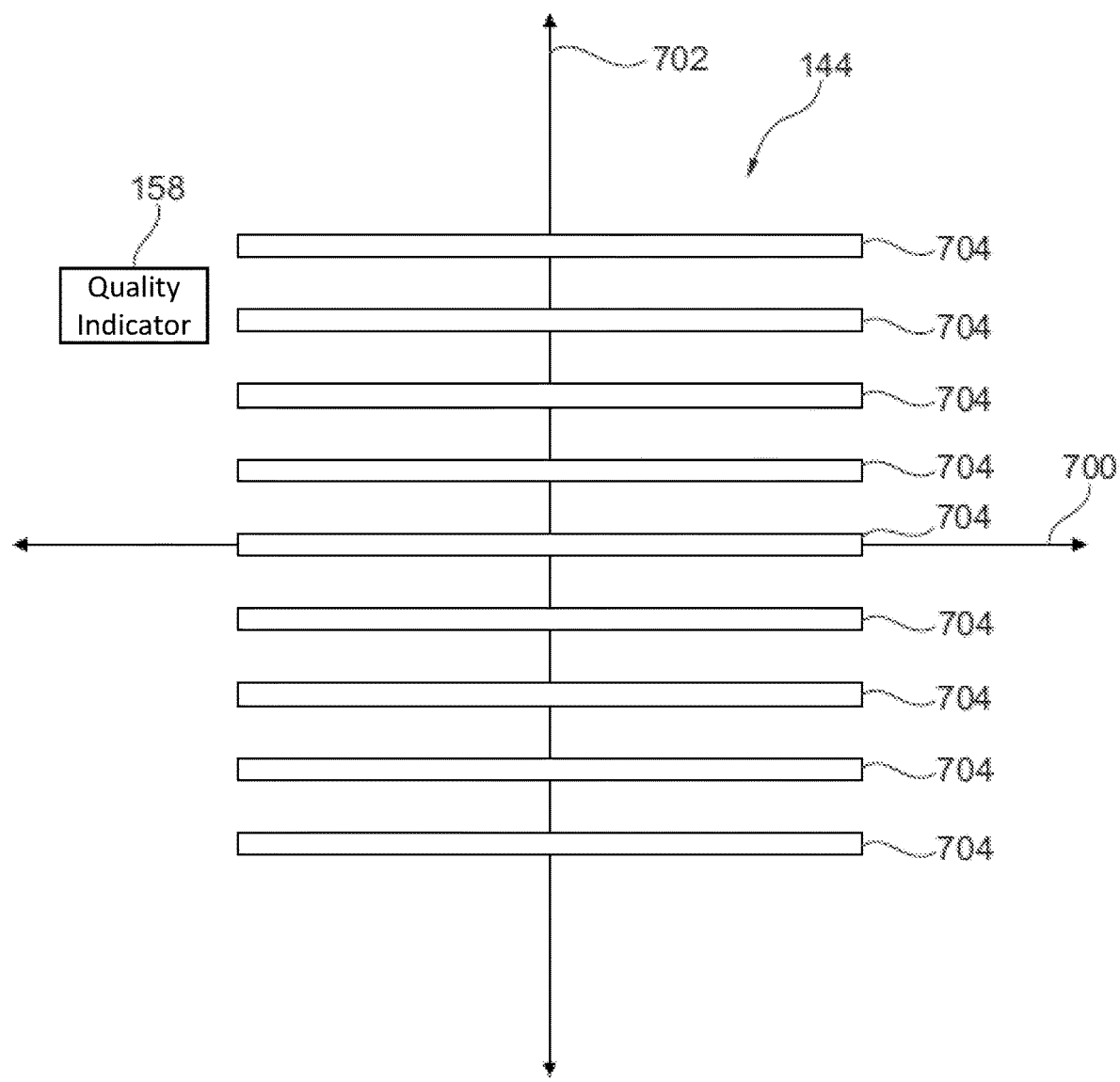
FIG. 7 illustrates an example of sampling patterns for magnetic resonance k-space data.

FIG. 7 illustrates an example of magnetic resonance k-space data 144. The magnetic resonance k-space data 144 is an example of magnetic resonance data. The example in FIG. 7 shows a rectilinear sampling pattern. For example, the axes 700 could represent $k_x$ and the axes 702 could represent $k_y$. The lines 704 indicate the sampling pattern. The magnetic resonance k-space data 144 has been labeled with a quality indicator 158. The quality indicator 158 is additional data which has been inserted into the k-space. In this example the quality indicator 158 is located in a higher value region of k-space than the k-space samples 704. In other examples the quality indicator could for example be interleaved or between two of the rows 704. The presence of the quality indicator 158 in the k-space data 144 has the effect of corrupting or partially corrupting any magnetic resonance images which are reconstructed from this magnetic resonance k-space data 144.

A specialized program for viewing or reconstructing the images from the magnetic resonance k-space data 144 could remove the quality indicator 158. For example, the quality indicator 158 could be placed in a standard location in k-space or there may be a header or other meta data accompanying the magnetic resonance k-space data that indicates the location of the quality indicator 158 and how to remove it. In other examples the quality indicator 158 could be added by using an algorithm and distributing the data. For example, distributing the data 158 may be used to add data which would result in particular geometric artifacts or indicators being present in any resulting magnetic resonance image. Such functionality could be implemented in the medical imaging system of FIG. 12, which is described below.

Figure 8:
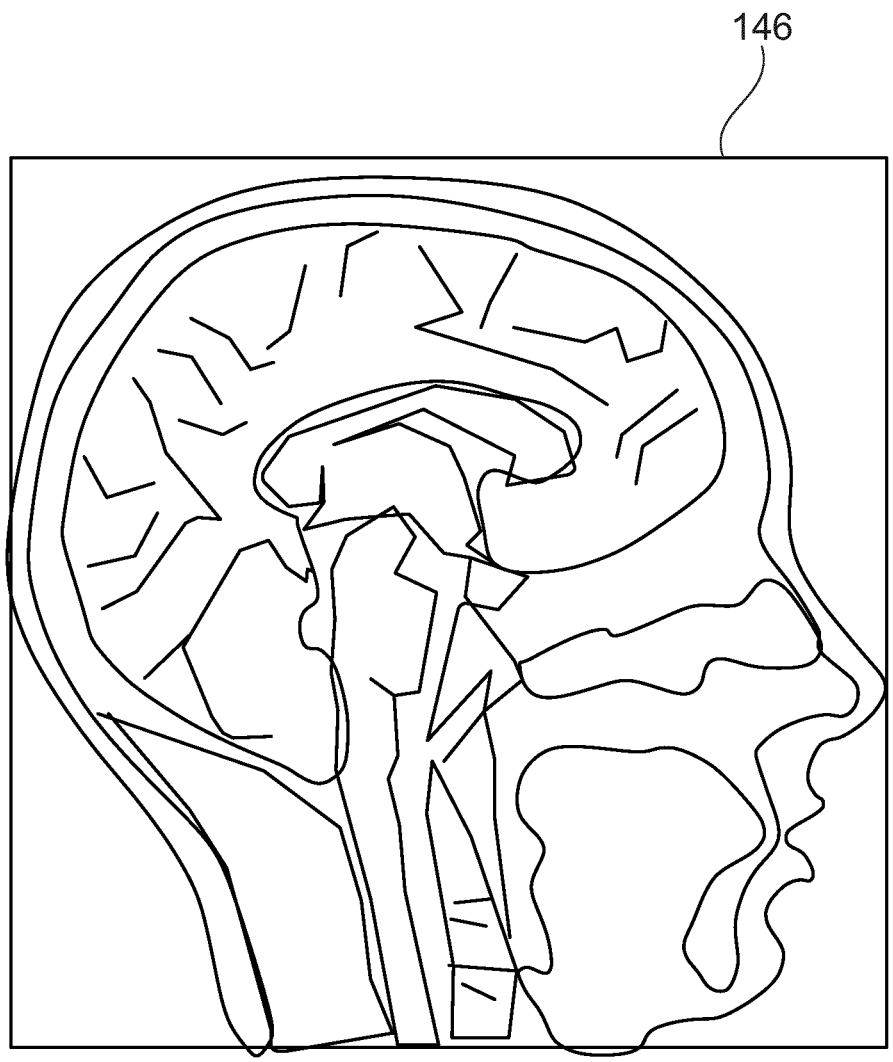
FIG. 8 shows a representation of magnetic resonance imaging data.

FIG. 8 shows a representation of magnetic resonance image data 146. The magnetic resonance image data 146 could for example be two- or three-dimensional datasets. The example in FIG. 8 essentially shows a rendering or representation of a rendering of magnetic resonance image data 146.

Figure 9:
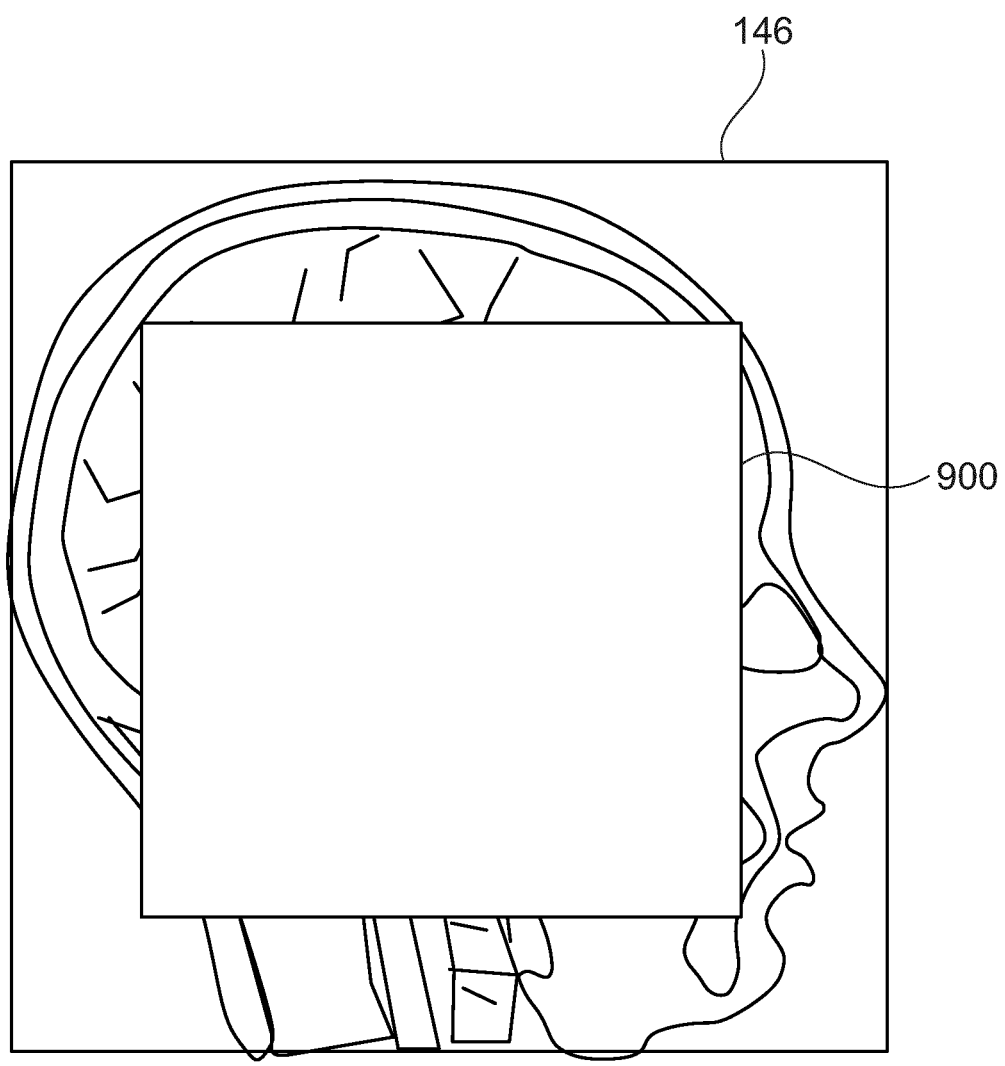
FIG. 9 shows the representation of magnetic resonance imaging data with an example of a visual indicator.

FIG. 9 is used to indicate one example of a visual indicator 900. FIG. 9 shows the same representation of the magnetic resonance image data 146 but in this case the image 146 also contains a visual indicator 900 which partially obscures the image 146. The visual indicator 900 could for example be implemented as a presentation state or as a watermark.

Figure 10:
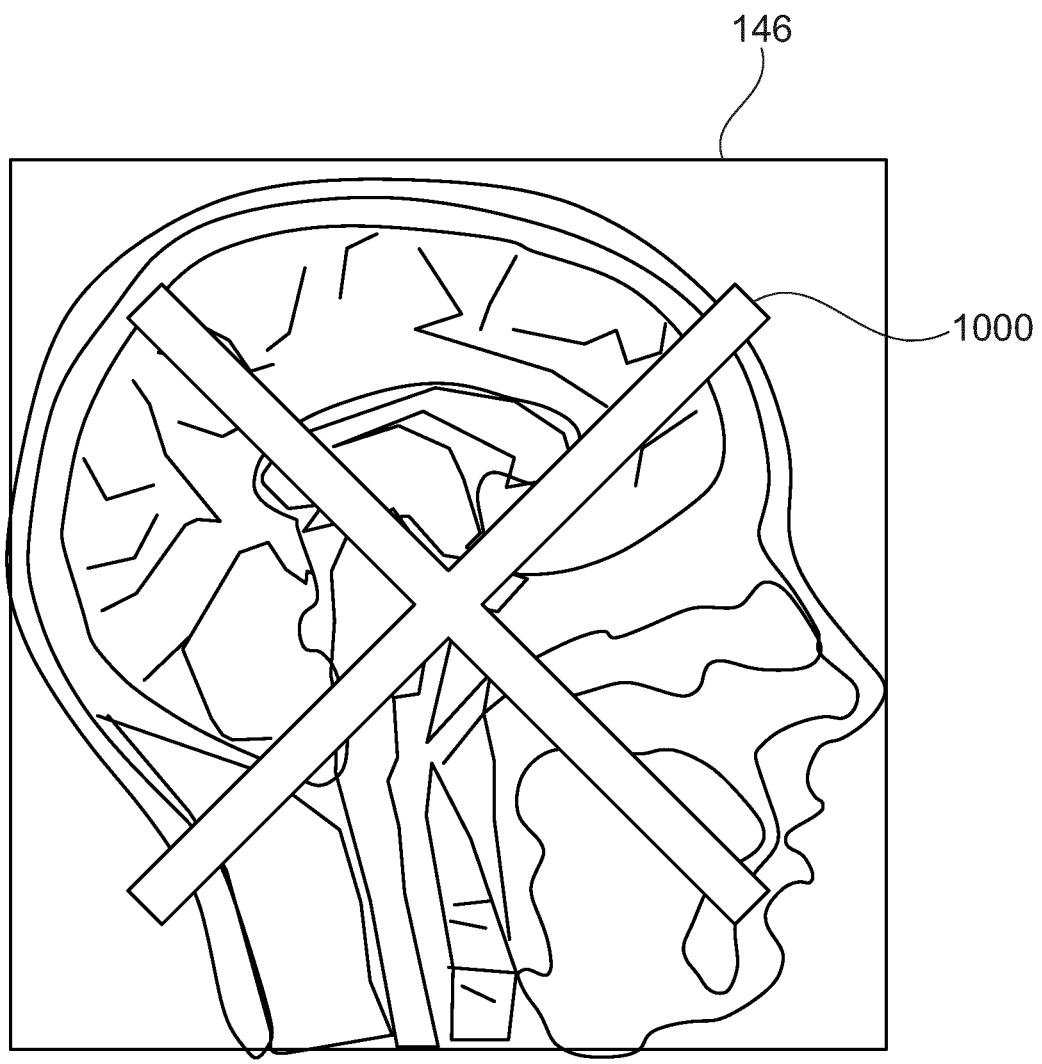
FIG. 10 shows the representation of magnetic resonance imaging data with a further example of a visual indicator.

FIG. 10 illustrates a further example of a visual indicator 1000. In FIG. 10 the representation of the magnetic resonance image data 146 is again shown. There is a large X-like structure superimposed on the image 146 which is intended to represent a symbol 1000 that has been used as a visual indicator. This symbol 1000 could for example be implemented again by using a presentation state in a DICOM file or it may also be implemented as a watermark.

Figure 11:
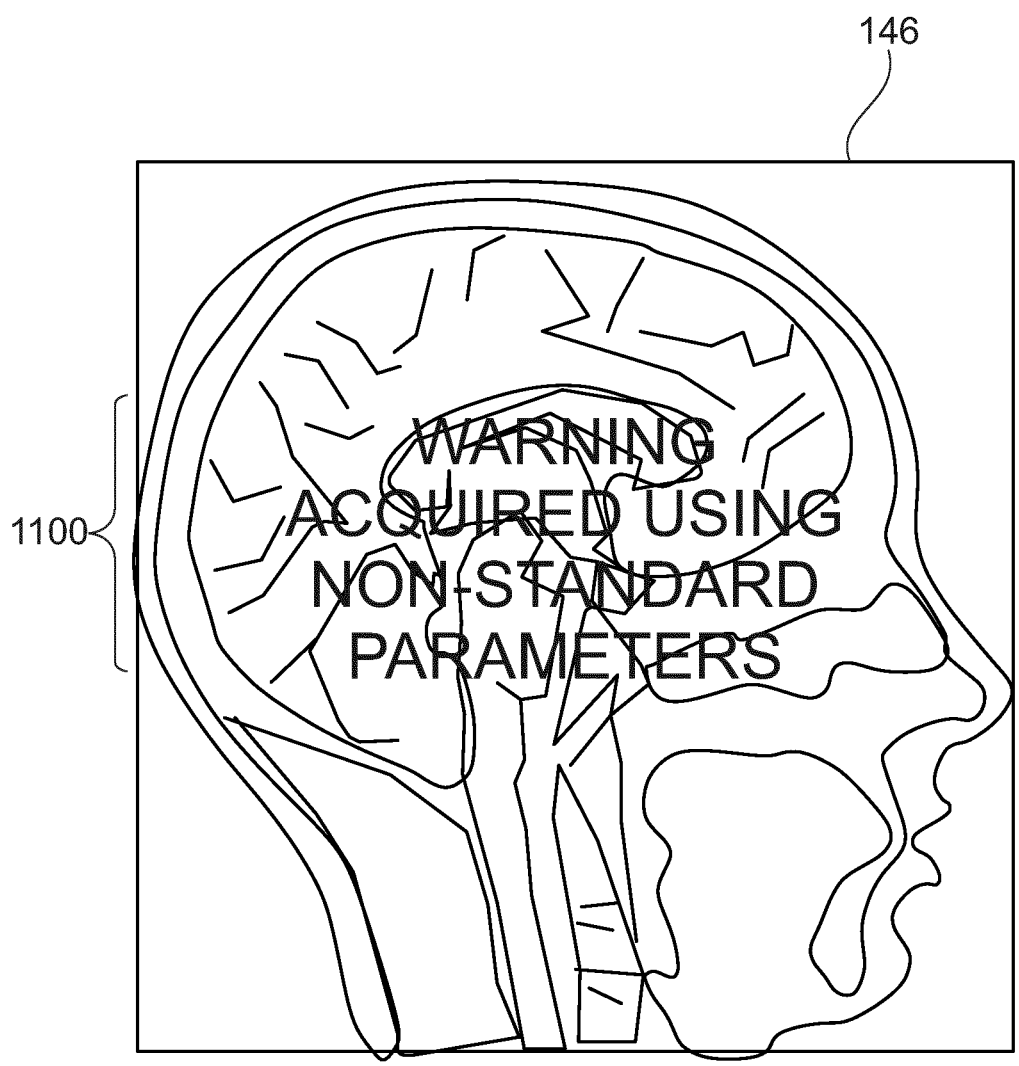
FIG. 11 shows the representation of magnetic resonance imaging data with a further example of a visual indicator.

FIG. 11 illustrates a further example of a visual indicator 1100. In this example, again, the representation of the magnetic resonance image data 146 is shown. Also shown is text 1100 which is superimposed on the image 146. The superimposed text 1100 may for example be implemented as a presentation state if the image 146 is in a DICOM file or for example as a watermark. The text 1100 shown in FIG. 11 is intended only as an example. The text message 1100 could be changed to provide specific details to a viewer. For example, the text message could display a message such as "deviates from Consensus Protocol NAME/ID," where NAME/ID is a specific name and identifier of a magnetic resonance imaging protocol.

Figure 12:
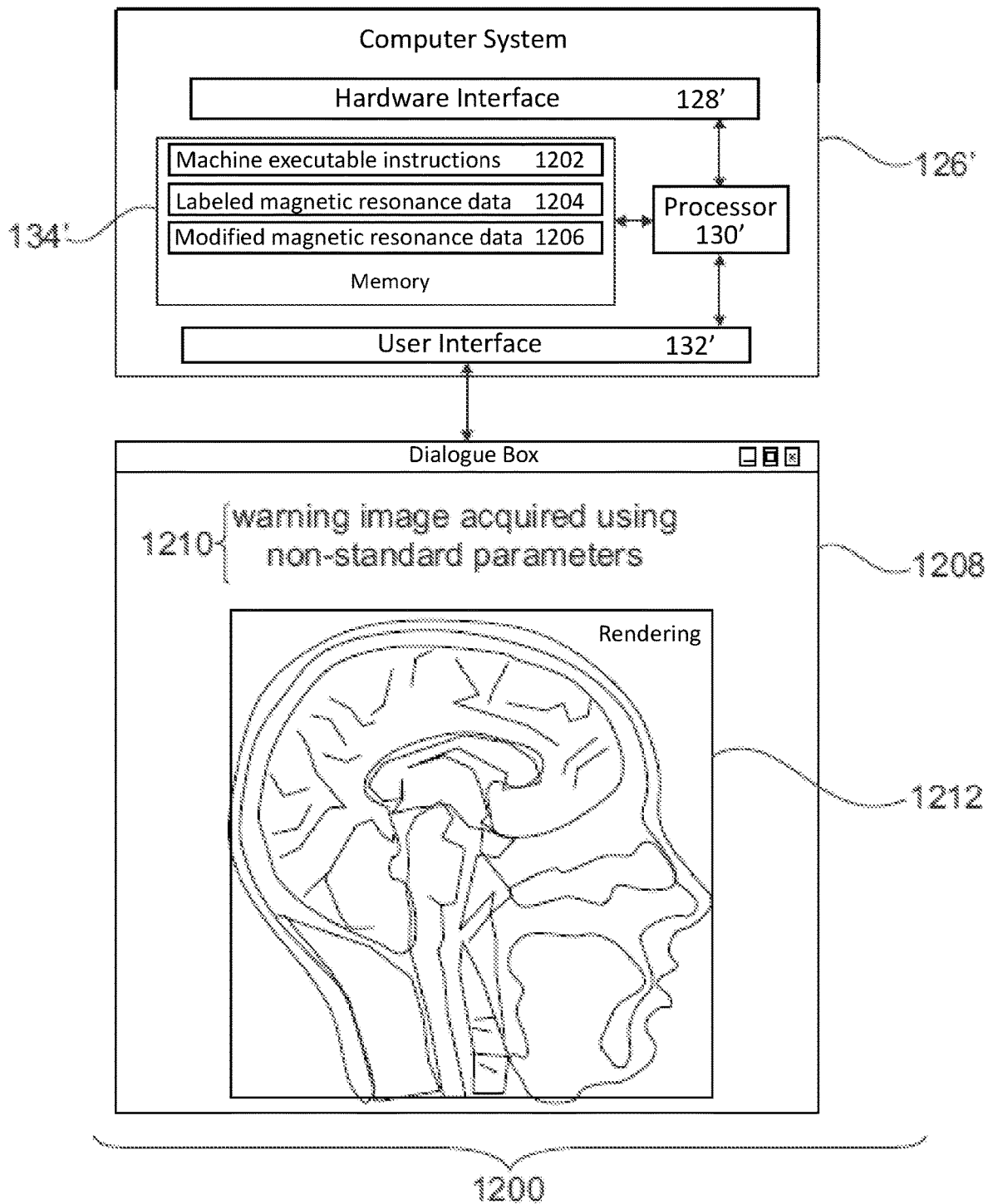
FIG. 12 illustrates an example of a medical imaging system.

FIG. 12 illustrates an example of a medical imaging system 1200. The medical imaging system comprises a computer system 126'. The computer system 126' comprises a processor 130' that is in communication with a network interface 128', a user interface 132', and a computer memory 134'. The computer memory 134' could for example be a non-persistent memory. The computer memory 134' is shown as containing machine-executable instructions 1202. The machine-executable instructions 1202 enable the processor 130' to perform various data processing and imaging tasks. The memory 134' is further shown as containing labeled magnetic resonance data 1204.

The labeled magnetic resonance data 1204 may for example be either image or k-space data that may possibly be encapsulated in a DICOM file. The memory 134' is further shown as containing a modified magnetic resonance data 1206 that has had the label removed. In this case the label is a quality indicator which is configured for causing a visible indicator in the magnetic resonance image such as is illustrated in any of FIG. 9, 10 or 11. The user interface 132' may for example comprise a display. On the display may be shown as dialogue box 1208 which shows a rendering of the modified magnetic resonance data 1212. It can be seen that the rendering 1212 does not have any visible indicators such as is shown in FIG. 9, 10 or 11. For example on the dialogue box 1208 there may be a warning 1210 which is displayed. As the warning 1210 is displayed there is no need to have the visual indicator shown on the rendering 1212.

Figure 13:
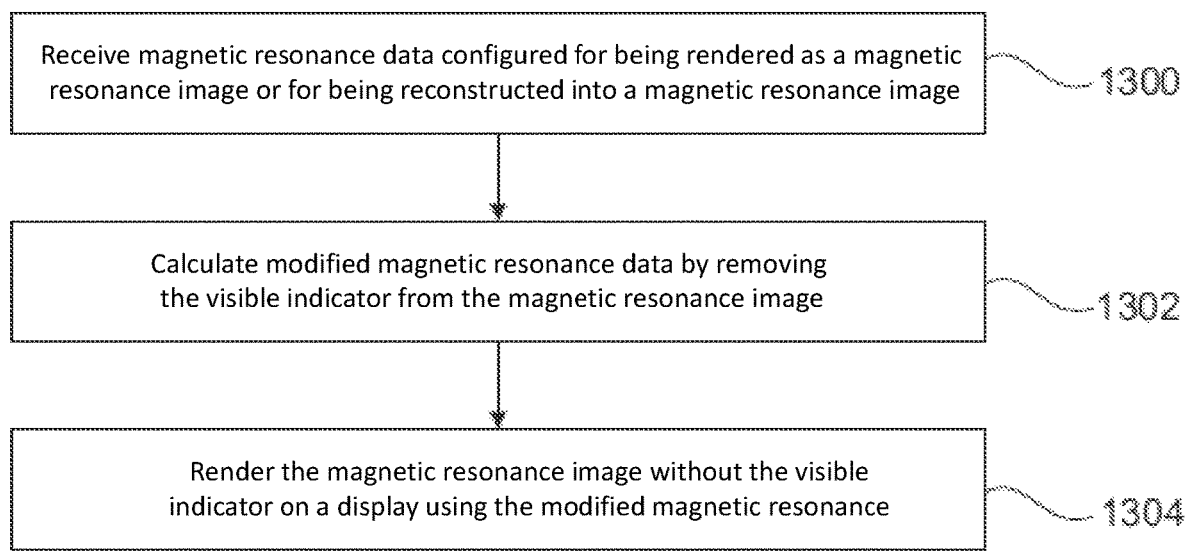
FIG. 13 shows a flow chart which illustrates an example of a method of operating the medical imaging system of FIG. 12.

FIG. 13 shows a flowchart which illustrates a method of operating the medical imaging system 1200 of FIG. 12. First in step 1300 the magnetic resonance data 1204 is received. The magnetic resonance data 1204 is configured for being rendered as a magnetic resonance image 1212 or for being reconstructed into the magnetic resonance image 1212. The magnetic resonance image comprises a quality indicator descriptive of whether one or more of the pulse sequence modification commands used to acquire the magnetic resonance data are outside of a parameter range. Examples of the visual indicator are shown in FIGS. 9, 10 and 11. The quality indicator is configured causing a visible indicator in the magnetic resonance image 1212. Next in step 1302 the modified magnetic resonance data 1206 is calculated by removing the visible indicator from the magnetic resonance image.

Next in step 1304 the magnetic resonance image 1212 is rendered without the visible indicator on a display 132' using the modified magnetic resonance data 1206. Depending on how the visible indicator is implemented there may be different means used to remove it. For example, if it is a presentation state the machine-executable instructions could cause the presentation state to be disabled or removed. In other cases, if the visible indicator is a watermark then an algorithm used to reverse the addition of the watermark may be executed. In some examples meta data or a file header may be used to provide information which may be used for removing the watermark.

In some examples there may be an additional state of deleting the modified magnetic resonance data 1206 whenever the dialogue box 1208 is closed. This may for example prevent the modified magnetic resonance data 1206 from being propagated without the quality indicator.

Figure 14:
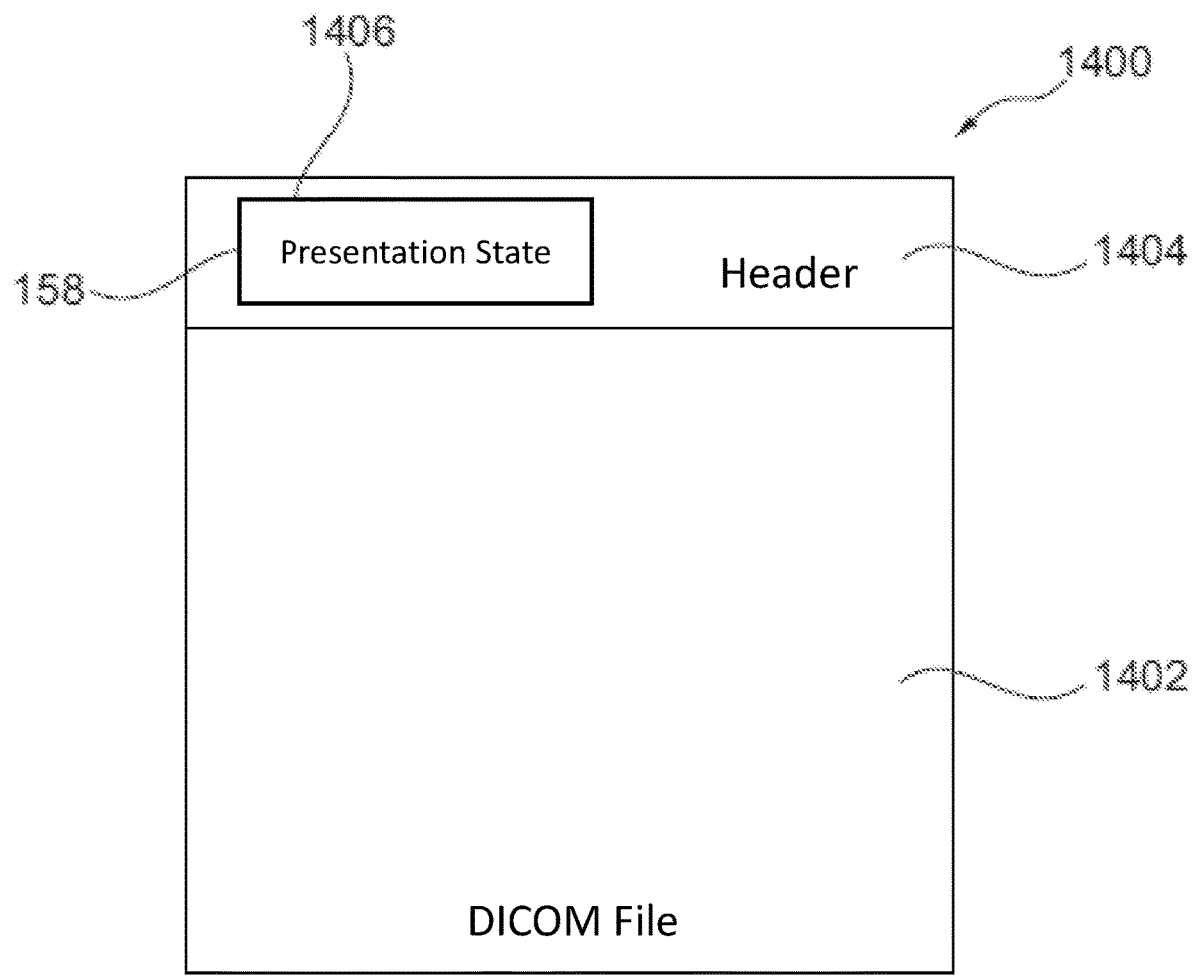
FIG. 14 shows a graphical representation of a DICOM file.

FIG. 14 shows an image which represents the structure of a DICOM file 1400. The DICOM file 1400 may comprise magnetic resonance data 1402 either in the form of raw k-space data or in image space having been already reconstructed. The magnetic resonance data 1402 is labeled with a quality indicator 158. In this case the quality indicator 158 is a presentation state 1406 contained in the header 1404. The presentation state 1406 may cause a visual indicator when the magnetic resonance image is rendered from the magnetic resonance data 1402.

Figure 15:
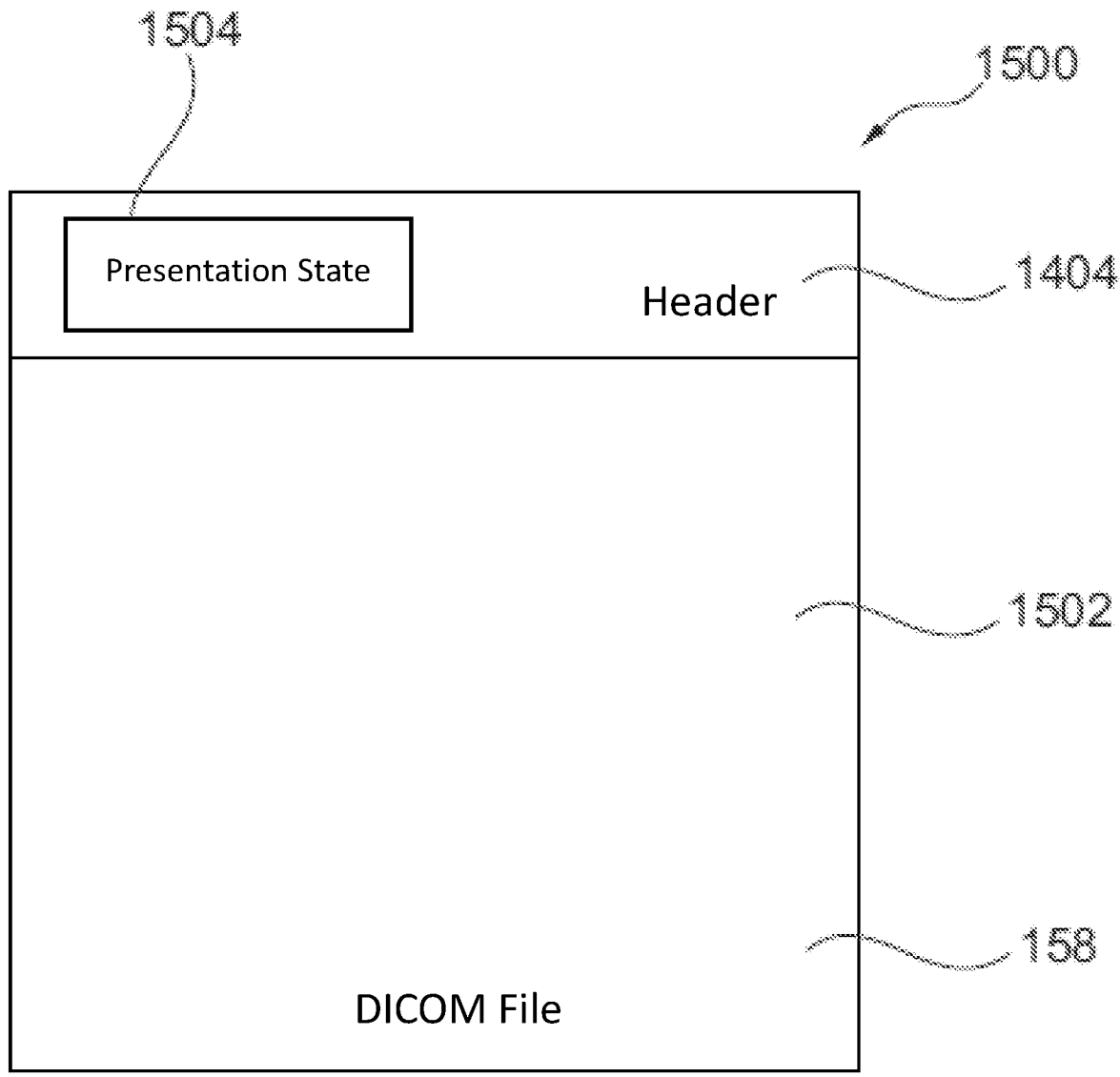
FIG. 15 shows a further graphical representation of a DICOM file.

FIG. 15 illustrates a further example of the structure of a DICOM file 1500. In this example there is magnetic resonance data 1502 that is an image space and has been watermarked. The quality indicator 158 is therefore at least partially part of the magnetic resonance data 1502. Within the header 1404 of the DICOM file 1500 is watermark removal data 1504. The watermark removal data 1504 is data which may be used for removing the watermark from the magnetic resonance data 1502 before rendering.

A strength of MRI technology is the flexibility and variability of parameter space in MRI pulse sequences and protocols constitutes a strength of the technology. When moving forward to accurate and reproducible images and especially for establishing quantitative techniques which relate to established baselines in population studies standardized sequences subject to a certain level of quality control are often adhered to. In practice, this may limit the flexibility of the sequence parameter space, or hampers ensuring that image data from multiple sequences in a protocol are consistent with those used for the established baseline methods.

Examples may provide for a more specific, (user) configurable, and extendible method is proposed to support quality control of MR sequences to conform consensus recommendations from professional societies, agreed requirements on allowed parameter ranges between suppliers of processing software and MR sequence developers, or diagnostic standards locally developed in hospitals (or hospital chains).

This method may include one or more of the following feature or steps:

Set the applicable qualifying parameter ranges in conformance with the required quality control conditions (Note: exploring parameter space beyond the ranges is allowed, but will (only) invalidate the sequence classification and identification)

Define the qualifying identification element, by the authenticated expert user. An example of such a qualifier is a free format string.

Display the qualification at the sequence or protocol level, prior to execution

Augment the image series with the defined qualifier string.

This can be added in front of the sequence name, and/or added into an additional data-element in the DICOM header.

Implement interpretation of the qualifier at the receiving software (post-processing).

In some examples, the image processing software or workstation may notify the user if unqualified data is received.

Sometimes, regulatory approvals are often limited to evaluated capabilities in a range of acquisition/sequence parameters. Going out of bound would invalidate the "CE mark" or other regulatory approval for a specific biomarker.

Nevertheless, such flexibility may be desirable or needed from a practice of medicine perspective (adapt to special patient needs), or to support research. For example, in the following situations examples would be useful when modifying the adjustable image acquisition parameters:

a. Amide Proton Transfer Imaging for gliomas: requires predefined settings for several parameters like B1+rms, labeling duration, readout sequence (TSE train, TE), number of offset frequencies, and primary offset.

Alternative settings may be useful for other pathologies (stroke) or to detect other exchangeable proton groups, but would invalidate the final image.

The range of allowable parameters to qualify the output color image/range against Sensitivity/Specificity claims from scientific literature are defined and lead to setting the attached label b. T1 MOLLI: several schemes exist in terms to inversion times and number of heart beats.

c. Quantitative ASL: inversion RF labeling efficiency is critical (B1+rms, and labeling duration) as well as inflow inversion time and number of such settings.

d. DIXON and DIXON Quant: 1st and 2nd TE values are critical to ensure adequate water/fat separation.

Examples may also be useful for informing users when modifying sequence parameter settings that they go out of bound. Some specific examples include:

a. brain volumetric analysis: requires a specific T1-weighted TFE protocol with certain resolution/TE/TR and allowed SENSE value. Image contrast is critical for the segmentation and volume determination of cortical structures b. Synthetic MR: a specific series of TE/TR/TI values and number of dynamic scans is required for accurate processing c. MR Elastography: several settings for the motion-encoding gradients (frequency, amplitude, direction) are required to relate the processing outcomes to scientific literature.

Other settings may be useful for clinical research but would disqualify the data from Sensitivity and Specificity claims.

d. 7D flow/vessel compliance assessment requires data acquired with a narrow range of flow encoding gradient settings Examples may also be useful for increasing diagnostic confidence in hospitals, medical professionals will establish MR sequences with preferred parameter settings. A certain range of variability will be allowed for resolution, and TE/TR parameters. When exceeding this range, the data will disqualify or contain a warning message.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS

- 100 magnetic resonance imaging system
- 104 magnet
- 106 bore of magnet
- 108 imaging zone
- 109 region of interest
- 110 magnetic field gradient coils
- 112 magnetic field gradient coil power supply
- 114 radio-frequency coil
- 116 transceiver
- 118 subject
- 120 subject support
- 126 computer system
- 126' computer system
- 128 hardware interface
- 128' network interface
- 130 processor
- 130' processor
- 132 user interface
- 132' user interface
- 134 computer memory
- 134' computer memory
- 140 machine executable instructions
- 142 pulse sequence recipe
- 144 magnetic resonance k-space data
- 146 magnetic resonance image data
- 148 adjustable image acquisition parameters
- 150 set of default parameter ranges
- 152 configuration commands
- 154 warning signal module
- 156 scan status command
- 158 quality indicator
- 200 warning dialogue box
- 202 warning
- 204 reject
- 206 continue
- 300 receive configuration commands configured for setting the adjustable image acquisition parameters of the pulse sequence recipe
- 302 determine if an out of range status exists by determining if any of the configuration commands are outside of the parameter range
- 304 provide a warning signal if the out range status exists
- 306 receive a scan status command from a user interface
- 308 acquire the magnetic resonance data by controlling the magnetic resonance imaging system using the pulse sequence recipe and the configuration commands if the scan status indicates an acceptance of the out of range status
- 310 label the magnetic resonance data with a quality indicator
- 312 write the magnetic resonance data with the quality indicator to a computer readable storage medium
- 400 parameter range change dialogue box module
- 402 range change data
- 500 parameter range change dialogue box
- 502 reject
- 504 continue
- 506 adjustable image acquisition parameter
- 508 boxes to enter parameter range
- 600 display a parameter range change dialogue box on the display
- 602 receive the range change data from the parameter range change dialogue box
- 604 modify the predetermined range for each of the one or more adjustable image acquisition parameters using the range change data
- 700 $k_x$
- 702 $k_y$
- 704 line of data in k-space
- 900 visual indicator which partially obscures image
- 1000 a symbol used as a visual indicator
- 1100 text used as a visual indicator
- 1200 medical imaging system
- 1202 machine executable instructions
- 1204 labeled magnetic resonance data
- 1206 modified magnetic resonance data
- 1208 dialogue box
- 1210 warning message
- 1212 rendering of modified magnetic resonance data
- 1300 receive magnetic resonance data is configured for being rendered as a magnetic resonance image or for being reconstructed into the magnetic resonance image
- 1302 calculate modified magnetic resonance data by removing the visible indicator from the magnetic resonance image
- 1304 render the magnetic resonance image without the visible indicator on a display using the modified magnetic resonance data
- 1400 DICOM file
- 1402 magnetic resonance data
- 1404 header
- 1406 presentation state
- 1500 DICOM file
- 1502 magnetic resonance data with watermark
- 1504 watermark removal data

The invention claimed is:

1. A magnetic resonance imaging system for acquiring magnetic resonance data of a subject within an imaging zone, wherein the magnetic resonance imaging system comprises:

a memory for storing machine executable instructions, wherein the memory stores one or more pulse sequence recipes configured for controlling the magnetic resonance imaging system to acquire the magnetic resonance data, wherein the memory further stores a set of parameter ranges for each of the one or more pulse sequence recipes, wherein at least a portion of the set of parameter ranges are user configurable, wherein the one or more pulse sequence recipes are configured for having one or more adjustable image acquisition parameters set to a default value, wherein the set of parameter ranges comprises a parameter range for the one or more adjustable image acquisition parameters; and a processor configured for controlling the magnetic resonance imaging system, wherein execution of the machine executable instructions causes the processor to:

receive configuration commands configured for setting the adjustable image acquisition parameters of a pulse sequence recipe selected from the one or more pulse sequence recipes;

determine if an out of range status exists by determining if any of the configuration commands are outside of the parameter range;

provide a warning signal if the out of range status exists;

receive a scan status command from a user interface;

acquire the magnetic resonance data by controlling the magnetic resonance imaging system using the pulse sequence recipe and the configuration commands if the scan status indicates an acceptance of the out of range status;

label the magnetic resonance data with a quality indicator descriptive of which of said adjustable image acquisition parameters are outside of the set of parameter ranges; and write the magnetic resonance data with the quality indicator to a computer readable storage medium.

2. The magnetic resonance imaging system of claim 1, wherein the quality indicator is configured for causing a visible indicator in the magnetic resonance data.

3. The magnetic resonance imaging system of claim 2, wherein the visible indicator is configured to do at least one a group consisting of: obscure a portion of the magnetic resonance image data, place a symbol in the magnetic resonance image data, place a text message in the magnetic resonance image data, place a text message that comprises an identifier of the pulse sequence recipe, reversibly corrupt the magnetic resonance data, or alter a file name of the magnetic resonance image data.

4. The magnetic resonance imaging system of claim 1, wherein the magnetic resonance data is magnetic resonance k-space data, wherein the magnetic resonance data is labeled by writing the quality indicator to a predetermined location in k-space within the magnetic resonance data.

5. The magnetic resonance imaging system of claim 1, wherein the magnetic resonance data is magnetic resonance image data.

6. The magnetic resonance imaging system of claim 5, wherein the quality indicator comprises watermark data configured for generating a visible watermark.

7. The magnetic resonance imaging system of claim 6, wherein the magnetic resonance data comprises a header, wherein execution of the machine executable instructions further causes the processor to write to the header watermark removal data for removal of the visible watermark.

8. The magnetic resonance imaging system of claim 1, wherein the magnetic resonance imaging system further comprises a display; wherein execution of the machine executable instructions further causes the processor to:

display a parameter range change dialogue box on the display, wherein the parameter range change dialogue box is configured for receiving range change data descriptive of changes to the parameter range for the one or more adjustable image acquisition parameters;

receive the range change data from the parameter range change dialogue box; and modify the predetermined range for each of the one or more adjustable image acquisition parameters using the range change data.

9. A non-transitory computer readable storage medium configured to store magnetic resonance data, wherein the magnetic resonance data is configured for being rendered as a magnetic resonance image or for being reconstructed into the magnetic resonance image, wherein the magnetic resonance data is obtained using a pulse sequence recipe, wherein the pulse sequence recipe has one or more adjustable image acquisition parameters, wherein the one or more adjustable image acquisition parameters have a corresponding set of parameter ranges, wherein the magnetic resonance data comprises a quality indicator descriptive of which of the one or more adjustable image acquisition parameters of the pulse sequence recipe are outside of the set of parameter ranges, and wherein the quality indicator is configured for causing a visible indicator in the magnetic resonance image.

10. The computer readable storage medium of claim 9, wherein magnetic resonance data is magnetic resonance k-space data, wherein the quality indicator is stored in a predetermined location in k-space within the magnetic resonance data.

11. The computer readable storage medium of claim 9, wherein the magnetic resonance data is magnetic resonance image data, wherein the quality indicator is configured to do any one of the following: obscure a predefined portion of the magnetic resonance image data, place a symbol in the magnetic resonance image data, place a text message in the magnetic resonance image data, reversibly corrupt the magnetic resonance data, and combinations thereof.

12. The computer readable storage medium of claim 11, wherein the quality indicator comprises watermark data configured for causing a visible watermark within the magnetic resonance image data.

13. The computer readable storage medium of claim 12, wherein the magnetic resonance data comprises a header, wherein the header comprises watermark removal data for removal of the visible watermark.

14. A medical imaging system comprising an imaging system memory and an imaging system processor, wherein the imaging system memory stores machine executable instructions, wherein execution of the machine executable instructions causes the processor to:

receive labeled magnetic resonance data configured for being rendered as a magnetic resonance image or for being reconstructed into the magnetic resonance image, wherein the magnetic resonance data is obtained using a pulse sequence recipe, wherein the pulse sequence recipe has one or more adjustable image acquisition parameters, wherein the one or more adjustable image acquisition parameters have a corresponding set of parameter ranges, wherein the magnetic resonance data comprises a quality indicator descriptive of which of the one or more adjustable image acquisition parameters of the pulse sequence recipe are outside of the set of parameter ranges, and wherein the quality indicator is configured for causing a visible indicator in the magnetic resonance image;

calculate modified magnetic resonance data by removing the visible indicator from the magnetic resonance image; and render the magnetic resonance image without the visible indicator on a display using the modified magnetic resonance data.

15. The medical imaging system of claim 14, wherein the modified magnetic resonance data is stored in a non-persistent memory.

16. The medical imaging system of claim 14, wherein the quality indicator comprises watermark data configured for causing a visible watermark within the magnetic resonance image data.

17. The medical imaging system of claim 16, wherein the magnetic resonance data comprises a header, wherein the header comprises watermark removal data, and wherein removing the visible indicator from the magnetic resonance image uses the watermark removal data in the header.

18. The medical imaging system of claim 14, wherein the magnetic resonance data is magnetic resonance k-space data, wherein the quality indicator is written in a predetermined location in k-space within the magnetic resonance data.

* * * * *